United States Patent [19]

Fraleigh

[11] 4,337,646
[45] Jul. 6, 1982

[54] OSCILLATING RHEOMETER DIE SET

[76] Inventor: M. Foster Fraleigh, 112 Lake Shore Dr., Old Port Cove Marina, North Palm Beach, Fla. 33408

[21] Appl. No.: 158,505

[22] Filed: Jun. 11, 1980

[51] Int. Cl.³ .................................................. G01N 11/14
[52] U.S. Cl. .................................................................. 73/59
[58] Field of Search ............................ 73/59, 15.4, 15.6

[56] References Cited

U.S. PATENT DOCUMENTS

| 2,076,816 | 4/1937 | Hess | 73/59 |
| 2,574,973 | 11/1951 | Hughes | 73/59 |
| 3,387,490 | 6/1968 | Wise | 73/15.6 |
| 3,494,172 | 2/1970 | Juve et al. | 73/59 |
| 3,681,980 | 8/1972 | Decker | 73/15.6 |
| 4,202,204 | 5/1980 | Hartert | 73/59 |

Primary Examiner—Anthony V. Ciarlante
Attorney, Agent, or Firm—Oldham, Oldham, Hudak & Weber Co.

[57] ABSTRACT

An oscillating rheometer die set is disclosed, having modifications to the lower die apparatus, the upper die apparatus, and the oscillator head. The purpose of these modifications include the creation of a sealing cavity of annular nature about the oscillator head, such that the elastomer sample is not encapsulated and once cured, may be easily removed from the cavity.

10 Claims, 4 Drawing Figures

4,337,646

OSCILLATING RHEOMETER DIE SET

BACKGROUND OF THE INVENTION

Heretofore, the use of rheometers to test the properties of elastomeric samples has utilized a cavity and rotor which have prevented the rapid removal of the cured elastomeric sample after the test has been completed. The elastomeric sample placed within the cavity, formed by the upper die apparatus and the lower die apparatus, has typically enveloped the rotor prior to the curing test. Once the elastomer has been cured, removal from the cavity is impeded by the cured elastomer about and around the rotator or rotor within the cavity. The rheometers having dies and rotators with this disadvantage include U.S. Pat. No. 3,681,980 and U.S. Pat. No. 3,387,490.

While it is of paramount importance to obtain sufficient surface contact between the rotator and the elastomeric sample for accurate measurement, it is necessary to prevent the envelopment of the rotator by the cured elastomeric sample which complicates and exacerbates the removal of elastomeric sample from the cavity of the rheometer testing instrument.

OBJECTS OF THE INVENTION

Consequently, it is an object of the invention to provide an improvement to the die apparatus of elastomeric testing instruments, wherein the interior surfaces of the lower die are modified to prevent the embedment or envelopment of the rotator in the elastomer after cure.

It is another object of the invention to provide an improvement to the oscillation mechanism of a testing instrument for elastomers, wherein the oscillator is modified to provide an outer circumferential surface which prevents elastomeric material from enveloping the oscillator.

These and other objects of the invention, which will become more apparent as the detailed description of the preferred embodiment proceeds, are achieved by an elastomeric testing device having a lower platen, facilitating rapid removal of cured elastomeric samples, comprising: (a) a stationary die ring secured to the surface of the lower platen, said die ring having an interior circumferential surface, defining an aperture, and a recessed portion on the lower area of said interior circumferential surface; (b) an oscillator having a head extending into said aperture, said head having an outer circumferential surface; (c) a means for sealing the elastomeric samples between said oscillator and said die ring at said recessed portion of said die ring; and the combined surfaces of said interior circumferential surface, said outer circumferential surface, and said sealing means forming an elastomeric annular cavity whereby the cured elastomer is confined to said elastomeric annular cavity.

The objects of the invention are further achieved by an elastomeric testing apparatus, comprising a stationary die ring having a recessed interior circumference, an oscillator head extending into said ring, and sealing means for elastomeric samples within said ring contacting said interior circumference and said oscillator head.

DESCRIPTION OF THE DRAWINGS

For an understanding of the scope of the invention, reference is had to the following drawings, wherein.

DETAILED DESCRIPTION OF THE PREFERRED EMBODIMENTS

Figure 1:
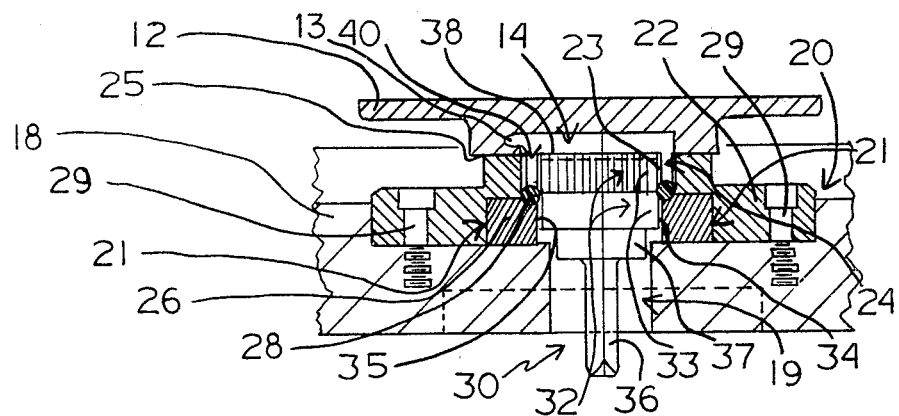
FIG. 1 is a cross-sectional view of the die apparatus and cavity, and a side view of the oscillator.

For an understanding of the scope of the best mode of this invention, reference is had to FIG. 1. FIG. 1 is a cross-sectional illustration of a portion of a rheometer, generally described as 10. This rheometer 10 is composed of an upper die assembly 12, a lower die assembly 20, a lower platen assembly 18, and an oscillator assembly 30. The upper die assembly 12 has an upper die recess 14 and is any conventional upper die assembly 12 known to those skilled in the art. Optionally, however, the upper die recess may have a crescent 13 extending arcuately along approximately 70° of the recess circumference, in order that elastomeric sample 15 may form a tab 11 to facilitate removal from the recess 14.

The lower die assembly 20 of the present invention resides in the lower platen assembly 18, which further has a lower platen aperture 19 from which oscillator assembly 30 protrudes. Once again, the conventional features of the lower platen assembly 18 are well known to those skilled in the art, as well as any other portions of the rheometer 10 not shown or described. The lower die assembly 20 and oscillator assembly 30 of the present invention may be used to retrofit existing rheometers available in the art, or assemblies 20 and 30 may be incorporated into the production of new rheometers 10.

The lower die assembly 20 of the present invention comprises a lower die ring 22, collar 26 and elastomeric sealing means 28.

The die ring 22 and collar 26 are constructed from metallic materials known to those skilled in the art. The elastomeric sealing means 28 may be formed as an O-ring, a circular gasket, or other similar object. It may be made from elastomers which withstand rheometer testing temperatures during repeated tests.

The lower die ring 22 is secured to the lower platen assembly 18 through fastener apertures 29, existing in a plurality about the perimeter of die ring 22. More importantly, lower die ring 22 is composed of an interior friction surface 23 which defines a lower die aperture 24 extending from engagement surface 25 with upper die assembly 12, to the lower platen assembly 18.

Figure 3:
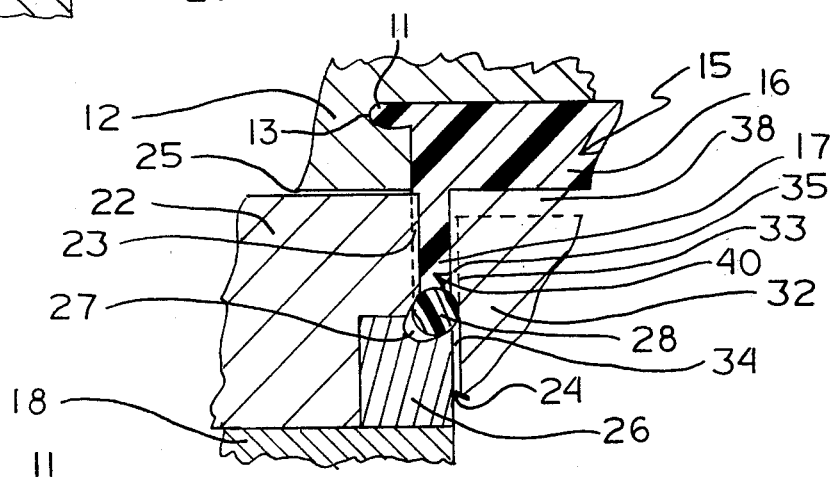
FIG. 3 is an alternative embodiment of the recess within which the elastomeric sealing means resides; and, FIG. 4 is an alternative embodiment of the annular cavity.
Figure 4:
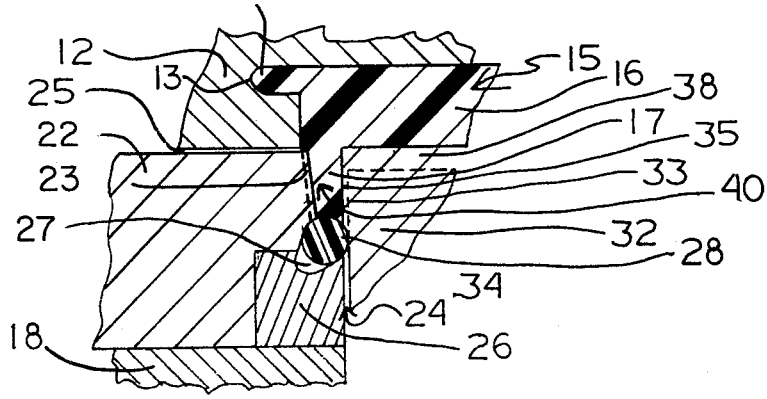

Referring to FIG. 1, the lower die ring 22, has a recessed lower portion 21 into which collar 26 is secured. Collar 26, which is preferably metallic, has a curved recess 27 upon which the elastomeric sealing means 28 secures. As seen in FIGS. 3 and 4, the recessed lower portion 21 and curved recess 27 may be modified to accommodate the elliptical deformation of the elastomeric sealing means 20 during operation of the rheometer 10. It has been found that a minimal amount of pressured contact is desired between the sealing means 28 and the oscillator assembly 30. Otherwise, pressure upon the oscillator assembly 30 would render inaccurate measurements of the elastomeric samples being tested. Therefore, to relieve any such potential pressure, the portion 21 and the recess 27 are expanded inwardly toward the lower die assembly 20, into which the deformed sealing means 28 may expand. It has also been determined that the minimal contact between means 28 and oscillator assembly 30 will maintain sealant qualities to prevent sample 15 from escaping beneath means 28 into the remainder of aperture 24.

The oscillator assembly 30 of the present invention comprises an oscillator head 32, and an oscillator shaft 36, made from materials known to those skilled in the art. The oscillator head 32 has an outer circumference 33 composed of a sealant surface 34 and a friction surface 35. The oscillator shaft 36 has an oscillator shaft shoulder 37 to provide sufficient surface area of interconnection between shaft 36 and head 32. The oscillator assembly 30, particularly oscillator head 32, protrudes from the lower platen aperture 19 of lower platen assembly 18.

The oscillator head 32 of the present invention extends into aperture 24 of the lower die ring 22. Preferably oscillator head 32 is cylindrical in shape. The outer circumference 33 of head 32 is divided into a sealant surface 34 which engages elastomeric sealing means 28, and a friction surface 35 which engages the elastomer sample 15 for testing purposes. The sealant surface 34 is of sufficient height to engage elastomeric sealing means 26 seated in the curved recess 27 of metallic collar 26.

Alterations to the shape of both assemblies 20 and 30 are necessary to achieve the objects of this invention. Because the cured elastomer is extremely difficult to remove from the rheometer testing instrument 10 when it envelops or closes the rotating member, it is crucial to prevent any elastomer from becoming cured at a position beneath the friction surface 35 of oscillator head 32. Consequently, the alterations to assemblies 20 and 30 create an annular cavity 40 created by the conjunction of friction surface 35, friction surface 23, and elastomeric sealing means 28. Annular cavity 40 may also be defined as the shape of aperture 24 as limited by the intrusion of oscillator head 32 beyond contact of sealant means 28 with sealant surface 34.

The elimination of any elastomer beneath the oscillator head 32 places the burden of oscillation of the elastomer sample 15 between friction surface 35 of the oscillator assembly 30 and interior friction surface 23. As may be seen by reference to FIG. 1, the surfaces 23 and 35 and upper surface 38 may optionally include a textured, serrated, nurled, or other partitioned surface to frictionally engage the elastomer during the rheometer test.

The rheometer testing apparatus measures differential stress in the interior of the elastomer sample 15. Any elastomeric resistance from means 28 distorts the measurement of sample 15. Therefore, minimal contact of sealant means 28 with sealant surface 34 is desired. Such minimal contact may be ensured by expanded space downwardly and inwardly in portion 21 and recess 27, as seen in FIGS. 3 and 4, to accomodate for the elliptical deformation of means 28 known by the inventor to occur. Relief of that elliptical deformation of means 28 is directed away from surfaces 23 and 35.

Figure 2:
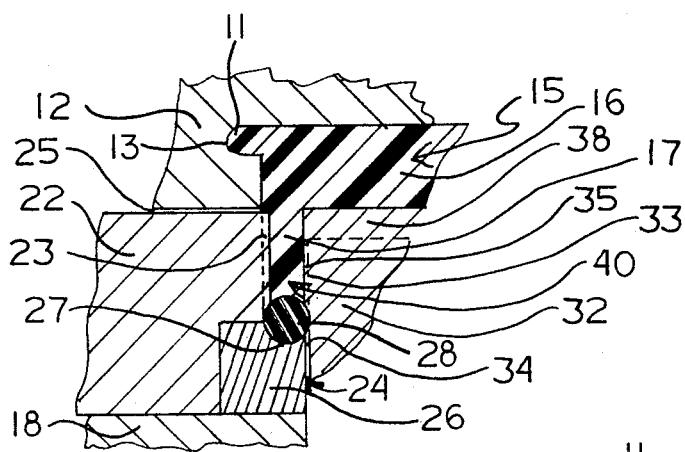
FIG. 2 is an enlarged view of the shape of the annular cavity.

Referring to FIG. 2, an enlarged view of the annular cavity 40 may be seen as defined in one embodiment. The friction surface 35 of the oscillator head 32 is shown to have a cylindrical shape. Likewise, the interior friction surface 23 of die ring 22 is substantially orthogonal to the surface of platen 18, thereby providing a cylindrical aperture 24. Alternatively stated, interior surface 23 and outer surface 35 are in a concentric relationship about an axis through the oscillator head 32. The result of this configuration provides an annular cavity 40 having parallel side surfaces. Because, in the preferred embodiment, elastomeric sealing means 28 such as an O-ring is seated on recess 27 of collar 26, the cavity 40 is reduced from the area defined by surfaces 23, 35 and means 28 to an area substantially seen in FIG. 2.

Whenever an elastomeric test sample 15 is placed within a rheometer 10, between upper die assembly 12 and lower die assembly 20, the elastomer 15 typically consists of a plug 16, filling recess 14, a tab 11 filling crescent 13, and an elastomeric annular flange 17 filling cavity 40. As the rheometer 10 continues its conventional functions, the oscillator assembly 30 oscillates and the elastomeric test sample 15 is heated. The measurement of physical properties of the elastomeric test sample 15 in the interior of plug 16 and annular flange 17 is accomplished by equipment such as described in U.S. Pat. No. 3,681,980. The duration, temperature, oscillating force and other parameters of testing are well known to those skilled in the art.

Once the test sample 15 has been cured and these properties recorded, the operator of the rheometer 10 must remove the test sample 15 from recess 14 and cavity 40. Where, in the past, as seen with reference to U.S. Pat. No. 3,681,980, the oscillating member was enveloped by the elastomeric test sample 15; according to the present invention, annular cavity 40 permits the rapid removal of the test sample 15 for additional elastomeric testing. The elastomeric annular flange 17, within cavity 40, is rapidly removed because no portion of the sample 15 extends beneath the oscillator head 32. It has been found that the longevity of these crucial pieces of the rheometer is improved when the elastomeric test sample 15 does not securely engage any surface 23, 35 or sealant means 28 at the designated time for removal.

As seen in FIG. 4, a modification to surfaces 23 of the present invention improves the removal characteristics of the elastomeric test sample 15 after curing and testing. The surface 23 is angled inwardly towards the junction of oscillator head 32 and sealing means 28.

Whenever surface 23 of stationary die ring 22 is angled inwardly, aperture 24, before oscillator assembly 30 is placed therewithin, assumes an inverse frustral shape. Given the various possibilities of the embodiments of the present invention, of assembly 20, the annular cavity 40 may have a constant radial depth, or a reducing radial depth as contributed by the slope of surface 23.

The assemblies 20 and 30 of the present invention are suitable for existing rheometer structures known to those skilled in the art, or assemblies 20 and 30 may be incorporated into rheometers contemplating improvements to other portions of the rheometer. Further, the assemblies 20 and 30 may be placed in newly-manufactured rheometers or retro-fitted into rheometers already in use. The assemblies 20 and 30 are preferred to be used as a unit modifying cavity 24, although it is conceivable that either assembly 20 or 30 may be used individually in a rheometer.

While according to the Patent Statutes, a best mode and preferred embodiment of the invention has been provided, it is to be understood that the invention is not to be limited thereto or thereby. Consequently, for an understanding of the scope of the present invention, reference is had to the claims.

What is claimed is:

1. An elastomeric testing device having a lower platen, facilitating rapid removal of cured elastomeric samples, comprising:
   a stationary die ring secured to the surface of the lower platen, said die ring having an interior circumferential surface defining an aperture, and a recessed portion on the lower area of said interior circumferential surface;
   a collar residing in said recessed portion, said collar having a recess therein;
   an oscillator having a head extending into said aperture, said head having an outer circumferential surface;
   a means for sealing the elastomeric samples between said oscillator and said die ring at said recessed portion of said die ring, said sealing means residing in said recess of said collar; and,
   the combined surfaces of said interior circumferential surface, said outer circumferential surface, and said sealing means forming an elastomeric annular cavity whereby the cured elastomer is confined to said elastomeric annular cavity.

2. An elastomeric testing device, having a lower platen, facilitating the rapid removal of cured elastomeric samples, according to claim 1, wherein said interior circumferential surface is angled toward the junction of said oscillator head and said sealing means to define an inverse frustral aperture.

3. An elastomeric testing device, having a lower platen, facilitating the rapid removal of cured elastomeric samples, according to claim 1, wherein said interior circumferential surface is orthogonal to the surface of the lower platen to define a cylindrical aperture.

4. An elastomeric testing device, having a lower platen, facilitating the rapid removal of cured elastomeric samples, according to claim 1, wherein said outer circumferential surface has a friction surface frictionally engaging the elastomer; and,
   wherein said outer circumferential surface further has a sealant surface slidably engaging said sealing means.

5. An elastomeric testing device, having a lower platen, facilitating the rapid removal of cured elastomeric samples, according to claim 4, wherein said friction surface is orthogonal to the surface of the lower platen to define a cylindrical oscillator head.

6. An elastomeric testing device, having a lower platen, facilitating the rapid removal of cured elastomeric samples, according to claim 1, wherein said recessed portion and said recess have an elliptical shape, angled inwardly, of greater dimension than said sealing means, whereby deformation of said sealing means during testing extends into said elliptical shape and minimizes increased pressure on said oscillator head.

7. An elastomeric testing apparatus comprising;
   a stationary die ring having a recessed interior circumference;
   an oscillator head extending into said ring;
   means for sealing elastomeric samples within said ring contacting said interior circumference and said oscillator head; and
   a collar residing in said recessed interior circumference, said collar having a recess within which said sealing means resides.

8. An elastomeric testing apparatus, according to claim 7, wherein said recessed interior circumference and said collar recess have an elliptical shape, angled inwardly, of greater dimension than said sealing means, whereby deformation of said sealing means during testing extends into said elliptical shape and minimizes increased pressure on said oscillator head.

9. An elastomeric testing apparatus, according to claim 7, further comprising an upper die ring having an interior circumferential surface defining a recess, said interior circumferential surface having a crescent extending arcuately along about 70° of said circumferential surface.

10. An elastomeric testing apparatus, comprising:
    a stationary die ring having a recessed interior circumference;
    an oscillator head extending into said ring;
    means for sealing elastomeric samples within said ring contacting said interior circumference and said oscillator head; and
    wherein said recessed interior circumference has an elliptical shape angled inwardly of greater dimension than said sealing means, whereby deformation of said sealing means during testing extends into said elliptical shape and minimizes increased pressure on said oscillator head.

* * * * *